(12) United States Patent
Mayes et al.

(10) Patent No.: US 6,680,408 B2
(45) Date of Patent: Jan. 20, 2004

(54) PROCESSES FOR THE PREPARATION OF α-SUBSTITUTED BENZYLNITROGUANIDINES

(75) Inventors: David M. Mayes, Overland Park, KS (US); Vijay C. Desai, Shawnee, KS (US); Eric Rivadeneira, Overland Park, KS (US)

(73) Assignee: Bayer Cropscience LP, Pittsburgh, PA (US)

( * ) Notice: Subject to any disclaimer, the term of this patent is extended or adjusted under 35 U.S.C. 154(b) by 34 days.

(21) Appl. No.: 10/175,639

(22) Filed: Jun. 20, 2002

(65) Prior Publication Data

US 2003/0236168 A1 Dec. 25, 2003

(51) Int. Cl.$^7$ ............................................. C07C 277/08
(52) U.S. Cl. ..................... 564/231; 564/237; 564/230
(58) Field of Search ................................. 564/231, 237

(56) References Cited

U.S. PATENT DOCUMENTS

| | | | |
|---|---|---|---|
| 4,594,092 A | 6/1986 | Speltz et al. | 71/77 |
| 4,639,268 A | 1/1987 | Arotin et al. | 71/105 |
| 4,804,780 A | 2/1989 | Speltz et al. | 564/104 |
| 4,944,788 A | 7/1990 | Speltz et al. | 71/88 |
| 5,175,365 A | 12/1992 | Arotin et al. | 564/105 |
| 6,160,126 A | * 12/2000 | Kando et al. | 548/477 |

* cited by examiner

*Primary Examiner*—Shailendra Kumar
(74) *Attorney, Agent, or Firm*—Richard E. L. Henderson; Joseph C. Gil

(57) ABSTRACT

Processes for preparing α-substituted benzylnitroguanidines include the steps of providing a reaction mixture comprising water, alcohol, an S-alkyl nitroisothiourea, and an α-substituted benzylamine; heating the reaction mixture; steam distilling the alcohol from the reaction mixture; and isolating an α-substituted benzylnitroguanidine from the remaining water layer.

20 Claims, No Drawings

PROCESSES FOR THE PREPARATION OF α-SUBSTITUTED BENZYLNITROGUANIDINES

The invention relates to processes for the preparation of α-substituted benzylnitroguanidines. The invention further relates to processes for isolation of α-substituted benzylnitroguanidines from aqueous alcoholic compositions.

BACKGROUND OF THE INVENTION

α-Substituted benzylnitroguanidines can be used as agricultural chemicals to increase crop yields, provide pre-emergent control of weeds, and promote defoliation. Controlled defoliation of plants has important agricultural uses. For example, cotton defoliation prior to harvest eliminates the main source of stain and trash, resulting in better grade cotton.

Speltz et al., U.S. Pat. Nos. 4,594,092, 4,804,780, and 4,944,788, teach the preparation of substituted benzylnitroguanidines by reacting a substituted benzylamine with 2-alkyl-1 (or 3)-nitro-2-thiopseudourea and isolating the solid product by filtration. Speltz et al. also teach the preparation of substituted benzylnitroguanidines by reacting a substituted benzylamine with N-alkyl-N-nitroso-N'-nitroguanidine in the presence of an aqueous aliphatic alcohol solution, followed by removal of the precipitate by filtration and washing of the solid product.

Arotin et al., U.S. Pat. Nos. 4,639,268 and 5,175,365, teach the preparation of substituted benzylnitroguanidines by reacting a substituted benzylamine with a 1-alkyl-3-nitro-1-nitrosoguanidine in the presence of an aqueous aliphatic alcohol solution, followed by removal of the precipitate by filtration and washing of the solid product.

Unfortunately, many prior art processes include steps of filtering and washing substituted benzylnitroguanidines, and such step can result in a loss of product. Additionally, many prior art processes require the use of large amounts of solvents.

There is a need for processes for preparing a-substituted benzylnitroguanidines which do not require the filtering and washing of the α-substituted benzylnitroguanidines. It would be desirable if the processes did not require the use of large amounts of solvents.

SUMMARY OF THE INVENTION

Accordingly, it is an object of the present invention to obviate problems of the prior art.

It is a further object of the present invention to provide processes for preparing α-substituted benzylnitroguanidines which do not require the filtering and washing of the α-substituted benzylnitroguanidines.

It is a another object of the present invention to provide processes for isolating α-substituted benzylnitroguanidines from aqueous alcoholic compositions which do not require the filtering and washing of the α-substituted benzylnitroguanidines According to one aspect of the invention there are provided processes for preparing α-substituted benzylnitroguanidines having the formula (I):

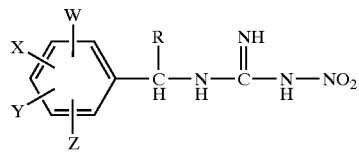

wherein R is an unsubstituted or an OH—or OCH$_3$-substituted C$_1$–C$_3$ alkyl, CH$_2$OCH$_3$, C$_6$H$_5$, CH$_2$C$_6$H$_5$, or CH$_2$CH=CH$_2$; and W, X, Y, Z are each individually hydrogen, halogen, OH, straight or branched chain C$_1$–C$_4$ alkyl, straight or branched chain C$_1$–C$_4$ alkoxy; CF$_3$, C(OH)$_2$CF$_3$, OCHF$_2$, OCF$_3$, NO$_2$, OCF$_2$CHF$_2$, N(CH$_3$)$_2$, CH$_2$N(CH$_3$)$_2$, CH$_2$NH$_2$, CH$_2$CH$_2$COOC$_2$H$_5$, C$_6$H$_4$, CH$_2$OH, CH$_2$OCH$_3$, COOCH$_3$, CH$_2$CH$_2$COOC$_2$H$_5$, OC$_6$H$_5$, OSO$_2$CH$_3$, SCH$_3$, CN, CH$_2$CN or tetrahydro-H-pyran-2-yl; and the salts, tautomers and optical isomers thereof.

The processes for preparing the α-substituted benzylnitroguanidines comprise the steps of:

(a) providing a reaction mixture comprising water, alcohol, an S-alkyl nitroisothiourea, and an α-substituted benzylamine;

(b) heating the reaction mixture;

(c) steam distilling the alcohol from the reaction mixture; and (d) isolating an α-substituted benzylnitroguanidine from the remaining water layer.

According to another aspect of the invention there are provided processes for preparing α-substituted benzylnitroguanidine, comprising the steps of:

(a) providing a reaction mixture comprising S-methyl nitroisothiourea, α-substituted benzylamine, water and alcohol;

(b) heating the reaction mixture;

(c) steam distilling the alcohol from the reaction mixture; and (d) filtering an α-substituted benzylnitroguanidine from the remaining water layer.

According to a further aspect of the invention there are provided processes for isolating of an α-substituted benzylnitroguanidine from a composition comprising water, alcohol and α-substituted benzylnitroguanidines, comprising the steps of:

(a) steam distilling the alcohol from the composition; and (b) filtering the 1-(α-ethylbenzyl)-3-nitroguanidine from the remaining water layer.

These and additional aspects, objects and advantages of the invention are more fully described in the following detailed description.

DETAILED DESCRIPTION

The present invention is directed to processes for the preparation of α-substituted benzylnitroguanidines and processes for isolation of α-substituted benzylnitroguanidines from aqueous alcoholic compositions.

The α-substituted benzylnitroguanidines which may be prepared using processes in accordance with the invention include compounds of the formula (I):

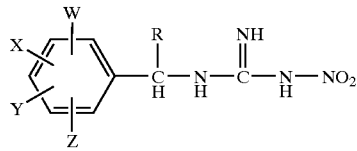

wherein R is a C$_1$–C$_3$ alkyl optionally substituted with OH or OCH$_3$;
CH$_2$OCH$_3$, C$_6$H$_5$, CH$_2$C$_6$H$_5$, or CH$_2$CH=CH$_2$; and W, X, Y, Z are each individually hydrogen, halogen, OH, straight or branched chain C$_1$–C$_4$ alkyl, straight or branched chain C$_1$–C$_4$ alkoxy; CF$_3$, C(OH)$_2$CF$_3$, OCHF$_2$, OCF$_3$, NO$_2$, OCF$_2$CHF$_2$, N(CH$_3$)$_2$, CH$_2$N (CH$_3$)$_2$, CH$_2$NH$_2$, CH$_2$CH$_2$COOC$_2$H$_5$, C$_6$H$_4$, CH$_2$OH, CH$_2$OCH$_3$, COOCH$_3$, CH$_2$CH$_2$COOC$_2$H$_5$, OC$_6$H$_5$, OSO$_2$CH$_3$, SCH$_3$, CN, CH$_2$CN or tetrahydro-H-pyran-2-yl; and the salts, tautomers and optical isomers thereof.

The α-substituted benzylnitroguanidine salts include inorganic salts, such as alkali metal, alkaline earth metal, Co, Cu, Zn, and Ag salts, and organic amine salts, such as ammonium compounds having the structure, N$^+$ R$_a$ R$_b$ R$_c$ R$_d$, wherein R$_a$, R$_b$, R$_c$, and R$_d$ are each independently selected from hydrogen and C$_1$–C$_{30}$ straight or branched chain alkyl optionally substituted with one or two OH, C$_3$–C$_6$ alkenyl or C$_3$–C$_6$ alkynyl groups. Preferred salts include the sodium, calcium, magnesium, potassium, ammonium, methylamine, trimethylamine, dodecylamine, tributylamine, diisopropylamine, triethylamine, tetrabutylamine, and tallow-amine salts of the substituted guanidine.

In one embodiment R is CH$_3$, C$_2$H$_5$, CF$_3$, n-C$_3$ H$_7$, CH$_2$OCH$_3$ or CH$_2$CH═CH$_2$. In another embodiment R is CH$_3$, CF$_3$, C$_2$H$_5$, or C$_6$H$_5$. In one preferred embodiment R is C$_2$H$_5$.

In one embodiment W, X, Y, Z are each individually hydrogen, halogen, OH, straight or branched chain C$_1$–C$_4$ alkyl, straight or branched chain C$_1$–C$_4$ alkoxy; CH$_2$OH, or CH$_2$OCH$_3$. In another embodiment W, X, Y, Z are each individually hydrogen, halogen, OH, OCH$_3$, OC$_2$H$_5$, OC$_3$H$_7$-n, OC$_4$H$_9$-sec, OCF$_3$, F, Cl, Br, I, CH$_3$, C$_2$H$_5$, CF$_3$, or CN. In one preferred embodiment W, X, Y and Z are all hydrogen.

In one embodiment the α-substituted benzylnitroguanidines prepared using processes in accordance with the invention are selected from the group consisting of (+)isomers, (−)-isomers and mixtures thereof of compounds having the formula (I) wherein R is CH$_3$, C$_2$ H$_5$, CF$_3$, n-C$_3$H$_7$, CH$_2$ OCH$_3$ or CH$_2$CH═CH$_2$; W is hydrogen, o-F, m-F, p-F, m-OCH$_3$, m-OH or p-Cl; and X, Y, and Z are all hydrogen, and the salts, tautomers and optical isomers thereof.

Examples of α-substituted benzylnitroguanidines include 1-(α-methylbenzyl)-3-nitroguanidine, 1-(α-ethylbenzyl)-3-nitroguanidine, 1-(α-ethyl-m-fluorobenzyl)-3-nitroguanidine, 1-(α-ethyl-m-methoxybenzyl)-3-nitroguanidine, 1-(o-fluoro-α-methylbenzyl)-3-nitroguanidine, 1-(p-fluoro-α-methylbenzyl)-3-nitroguanidine, 1-(α-trifluoromethylbenzyl)-3-nitroguanidine, 1-(α-propylbenzyl)-3-nitroguanidine, 1-(α-methyoxymethyllbenzyl)-3-nitroguanidine, and 1-(α-allylbenzyl)-3-nitroguanidine.

In one preferred embodiment the α-substituted benzylnitroguanidine compound is 1-(α-ethylbenzyl)-3-nitroguanidine. The 1-(α-ethylbenzyl)-3-nitroguanidine may be the (+) isomeric form, the (−) isomeric form or a mixture of the (+) and (−) isomeric forms. In a more preferred embodiment the guanidine compound is (+)-1-(α-ethylbenzyl)-3-nitroguanidine.

The α-substituted benzylnitroguanidine is formed by reacting an S-alkyl nitroisothiourea with α-substituted benzylamine, as set forth in the reaction below:

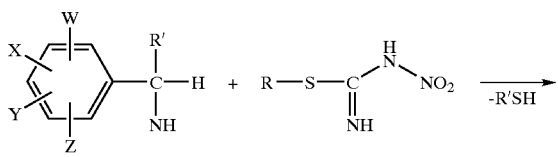

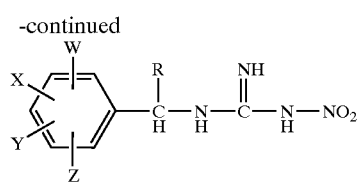

Processes in accordance with the present invention comprise the step of preparing a reaction mixture comprising water, alcohol, an S-alkyl nitroisothiourea and an α-substituted benzylamine having the formula (II)

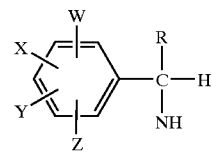

wherein R is a C$_1$–C$_3$ alkyl optionally substituted with OH or OCH$_3$; CH$_2$OCH$_3$, C$_6$H$_5$, CH$_2$C$_6$H$_5$, or CH$_2$CH═CH$_2$; and W, X, Y, Z are each individually hydrogen, halogen, OH, straight or branched chain C$_1$–C$_4$ alkyl, straight or branched chain C$_1$–C$_4$ alkoxy; CF$_3$, C(OH)$_2$CF$_3$, OCHF$_2$, OCF$_3$, NO$_2$, OCF$_2$CHF$_2$, N(CH$_3$)$_2$, CH$_2$N(CH$_3$)$_2$, CH$_2$NH$_2$, CH$_2$CH$_2$COOC$_2$H$_5$, C$_6$H$_4$, CH$_2$OH, CH$_2$OCH$_3$, COOCH$_3$, CH$_2$CH$_2$COO OC$_6$H$_5$, OSO$_2$CH$_3$, SCH$_3$, CN, CH$_2$CN or tetrahydro-H-pyran-2-yl; heating the reaction mixture; steam distilling the alcohol from the reaction mixture; and filtering the α-substituted benzylnitroguanidine from the remaining water layer.

In one embodiment the α-substituted benzylamine has the formula (II) wherein R is CH$_3$, C$_2$H$_5$, CF$_3$, n-C$_3$ H$_7$, CH$_2$OCH$_3$ or CH$_2$CH═CH$_2$, preferably CH$_3$, CF$_3$, C$_2$H$_5$, or C$_6$H$_5$, more preferably R is C$_2$H$_5$. In one embodiment W, X, Y, Z are each individually hydrogen, halogen, OH, straight or branched chain C$_1$–C$_4$ alkyl, straight or branched chain C$_1$–C$_4$ alkoxy; CH$_2$OH, or CH$_2$OCH$_3$, while in another embodiment W, X, Y, Z are each individually hydrogen, halogen, OH, OCH$_3$, OC$_2$H$_5$, OC$_3$H$_7$-n, OC$_4$H$_9$-sec, OCF$_3$, F, Cl, Br, I, CH$_3$, C$_2$H$_5$, CF$_3$, or CN. Preferably W, X, Y and Z are all hydrogen.

In one embodiment the α-substituted benzylamine has the formula (II) wherein R is CH$_3$, C$_2$ H$_5$, CF$_3$, n-C$_3$H$_7$, CH$_2$OCH$_3$ or CH$_2$CH═CH$_2$; W is hydrogen, o-F, m-F, p-F, m-OCH$_3$, m-OH or p-Cl; and X, Y, and Z are all hydrogen, and the salts, tautomers and optical isomers thereof. In one preferred embodiment the α-substituted benzylamine is α-ethylbenzyl-amine.

Suitable S-alkyl nitroisothiourea include S-C$_1$–C$_4$-alkyl nitroisothio-urea, preferably S-methyl nitroisothiourea.

Alcohols suitable for use in processes in accordance with the invention include aliphatic alcohols such as methanol, ethanol and propanol and combinations thereof. Ethanol and combinations of ethanol with other aliphatic alcohols are preferred, and the use of ethanol alone is most preferred. The water and the alcohol together form a solvent comprising from about 3% to about 80%, more preferably 5% to about 60%, by volume water and from about 20% to about 97%, more preferably about 40% to about 95%, by volume alcohol. In one embodiment of the invention the alcohol is ethanol, and the solvent comprises about 5% water and about 95% ethanol.

Processes in accordance with the invention are advantageous in that large amounts of alcohol are not required. As used herein, "large amounts of alcohol" is intended to refer to a level of more than about 1 kilogram of alcohol per mole of S-alkyl nitroisothiourea.

In one embodiment of the invention the reaction mixture comprises less than about 700, preferably less than about 500, more preferably less than about 300, grams alcohol per mole of S-alkyl nitroisothiourea. In one embodiment of the invention the reaction mixture comprises less than about 200, preferably less than about 175, grams water per mole of S-alkyl nitroisothiourea.

Any suitable reactor may be used for preparing and heating the reaction mixture. In one embodiment the reactor is fitted with a vent line to an agent which can capture or absorb the alkyl mercaptan released during the reaction, preferably the reactor is fitted with a vent line to an aqueous caustic solution which absorbs the alkyl mercaptan. Suitable caustic solutions include solutions comprising water and a base selected from the group consisting of alkali metal hydroxides and combinations thereof. The caustic solution may comprise from about 10% to about 30% base.

The reaction mixture may be prepared by charging the reaction with the s-alkyl nitroisothiourea, water and alcohol, and adding the α-substituted benzylamine at a rate such that the reaction mixture remains at a temperature of no more than about 80° C., preferably less than about 40° C., more preferably less than about 30° C., throughout the addition of the α-substituted benzylamine. The react mixture may be stirred at temperature of no more than about 80° C., preferably less than about 40° C., more preferably less than about 30° C., for a period of time of from about 10 to about 60 minutes, preferably from about 20 to about 40 minutes, more preferably about 30 minutes prior to heating.

The step of heating the reaction mixture typically comprises heating the reaction mixture to a time and for a time sufficient for the α-substituted benzylnitroguanidine to be formed. In one embodiment the reaction mixture is heated to reflux, and maintained at reflux for a period of from about 1 to about 8 hours, preferably from about 4 to about 6 hours.

Any suitable steam distillation apparatus may be used for steam distilling the alcohol from the reaction mixture. The alcohol that is removed by the steam distillation may be purified, dried and recycled.

Removal of the alcohol results in a remaining water layer which comprises the α-substituted benzylnitroguanidine. The α-substituted benzylnitroguanidine may be isolated from the water layer using any suitable procedure, such as filtration. Any suitable filtration apparatus may be used for filtering the α-substituted benzylnitroguanidine from the water layer. The step of filtering the α-substituted benzylnitroguanidine from the water layer may be performed at atmospheric pressure or under vacuum. Suitable pressures for filtering are from about 150 to about 750 mm Hg, preferably from about 150 to about 400 mm Hg, more preferably from about 150 to about 250 mm Hg.

The steps of steam distilling and isolating the α-substituted benzylnitroguanidines from water, preferably by filtering, are not limited to synthesis methods using S-alkyl nitroisothiourea and α-substituted benzylamine. The steps may be used to isolate α-substituted benzylnitroguanidines from any aqueous alcoholic composition.

EXAMPLE

A 3000 ml 4-neck round bottom flask is fitted with a thermometer, reflux condenser, addition funnel, mechanical agitator and a vent line to an aqueous caustic solution. The aqueous caustic solution absorbs methyl mercaptan released during the reaction. The round bottom flask is charged with S-methyl nitroisothiourea (306 g, 2.24 moles) and 95% ethanol (980 g). α-ethylbenzylamine (297.1 g, 2.18 moles) is added via a dropping funnel at a rate such that the reaction mixture remains below 30° C. throughout the addition. The addition is completed in about 1 hour. The mixture is then cooled to room temperature and may be seeded with a few crystals of the product. The mixture is then stirred for about 4 hours.

When the product is isolated from the reaction mixture by prior art methods filtering the ethanol-containing mixture, washing the filtered product with 100 ml of 50% aqueous ethanol two times and then drying under vacuum to constant weight, the yield is from about 80% to 82%, by weight.

When, in accordance with the invention, the product is isolated from the reaction mixture by steam distilling the ethanol and then filtering the product from the remaining water layer, the yield is from about 90 to 94%, by weight.

Additional embodiments and modifications within the scope of the claimed invention will be apparent to one of ordinary skill in the art. Accordingly, the scope of the present invention shall be considered in terms of the following claims, and is understood not to be limited to the details of the methods described in the specification.

What is claimed is:

1. A process for preparing an α-substituted benzylnitroguanidine selected from the group consisting of α-substituted benzylnitroguanidines having the formula (I):

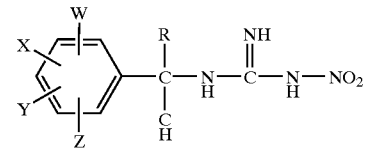

wherein R is an unsubstituted or an OH- or OCH$_3$-substituted C$_1$–C$_3$ alkyl, CH$_2$OCH$_3$, C$_6$H$_5$, CH$_2$C$_6$H$_5$, or CH$_2$CH=CH$_2$; and W, X, Y, Z are each individually hydrogen, halogen, OH, straight or branched chain C$_1$–C$_4$ alkyl, straight or branched chain C$_1$–C$_4$ alkoxy; CF$_3$, C(OH)$_2$CF$_3$, OCHF$_2$, OCF$_3$, NO$_2$, OCF$_2$CHF$_2$, N(CH$_3$)$_2$, CH$_2$N(CH$_3$)$_2$, CH$_2$NH$_2$, CH$_2$CH$_2$COOC$_2$H$_5$, C$_6$H$_4$, CH$_2$OH, CH$_2$OCH$_3$, COOCH$_3$, CH$_2$CH$_2$COOC$_2$H$_5$, OC$_6$H$_5$, OSO$_2$CH$_3$, SCH$_3$, CN, CH$_2$CN or tetrahydro-H-pyran-2-yl; and the salts, tautomers and optical isomers thereof;

the process comprising the steps of:
(a) providing a reaction mixture comprising water, alcohol, an S-alkyl nitroisothiourea, and an α-substituted benzylamine having the structure

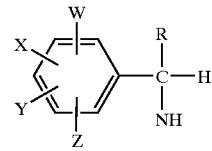

wherein R, W, X, Y and Z are as defined above;
(b) heating the reaction mixture;
(c) steam distilling the alcohol from the reaction mixture; and
(d) isolating an α-substituted benzylnitroguanidine from the remaining water layer.

2. A process according to claim 1, wherein the S-alkyl nitroisothiourea is an S-C$_1$–C$_4$-alkyl nitroisothiourea.

3. A process according to claim 2, wherein the S-C$_1$–C$_4$-alkyl nitroisothiourea is S-methyl nitroisothiourea.

4. A process according to claim 1, wherein R is $CH_3$, $C_2H_5$, $CF_3$, n-$C_3H_7$, $CH_2OCH_3$ or $CH_2CH=CH_2$.

5. A process according to claim 1, wherein W, X, Y, Z are each individually hydrogen, halogen, OH, straight or branched chain $C_1$–$C_4$ alkyl, straight or branched chain $C_1$–$C_4$ alkoxy; $CH_2OH$, or $CH_2OCH_3$.

6. A process according to claim 1, wherein W, X, Y, Z are each individually hydrogen, halogen, OH, $OCH_3$, $OC_2H_5$, $OC_3H_7$-n, $OC_4H_9$-sec, $OCF_3$, F, Cl, Br, I, $CH_3$, $C_2H_5$, $CF_3$, or CN.

7. A process according to claim 1, wherein R is $CH_3$, $CF_3$, $C_2H_5$, or $C_6H_5$ and W, X, Y and Z are all hydrogen.

8. A process according to claim 7, wherein the α-substituted benzylamine is α-ethylbenzylamine and the α-substituted benzylnitroguanidine is 1-(α-ethylbenzyl)-3-nitroguanidine.

9. A process according to claim 1, wherein the alcohol is ethanol and the reaction mixture comprises less than about 700 grams alcohol per mole of S-alkyl nitroisothiourea.

10. A process according to claim 1, wherein the reaction mixture comprises less than about 200 grams water per mole of S-alkyl nitroisothiourea.

11. A process according to claim 1, wherein the step of heating the reaction mixture comprises heating the reaction mixture to reflux, and maintaining the reaction mixture at reflux for a period of from about 1 to about 8 hours.

12. A process for preparing an α-substituted benzylnitroguanidine, comprising the steps of:

(a) providing a reaction mixture comprising S-methyl nitroisothiourea, α-substituted benzylamine, water and alcohol;

(b) heating the reaction mixture;

(c) steam distilling the alcohol from the reaction mixture; and (d) filtering an α-substituted benzylnitroguanidine from the remaining water layer.

13. A process according to claim 12, wherein the α-substituted benzylamine is α-ethylbenzylamine and the α-substituted benzylnitroguanidine is 1-(α-ethylbenzyl)-3-nitroguanidine.

14. A process according to claim 13, wherein the alcohol is ethanol.

15. A process according to claim 13, wherein the reaction mixture comprises less than about 700 grams alcohol per mole of S-methyl nitroisothiourea.

16. A process according to claim 15, wherein the reaction mixture comprises less than about 200 grams water per mole of S-methyl nitroisothiourea.

17. A process according to claim 13, wherein the step of heating the reaction mixture comprises heating the reaction mixture to reflux, and maintaining the reaction mixture at reflux for a period of from about 1 to about 8 hours.

18. A process according to claim 12, wherein the α-substituted benzylnitroguanidine is (+)1-(α-ethylbenzyl)-3-nitroguanidine.

19. A process for isolating of an α-substituted benzylnitro-guanidine from a composition comprising water, alcohol and α-substituted benzylnitroguanidines, comprising the steps of:

(a) steam distilling the alcohol from the composition; and (b) filtering the 1-(α-ethylbenzyl)-3-nitroguanidine from the remaining water layer.

20. A process according to claim 19, wherein the α-substituted benzylnitroguanidine is selected from the group consisting of α-substituted benzylnitroguanidines having the formula (I):

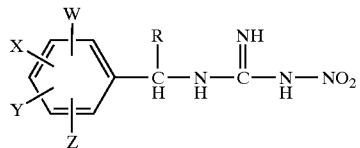

wherein R is an unsubstituted or an OH—or $OCH_3$-substituted $C_1$–$C_3$ alkyl, $CH_2OCH_3$, $C_6H_5$, $CH_2C_6H_5$, or $CH_2CH=CH_2$; and W, X, Y, Z are each individually hydrogen, halogen, OH, straight or branched chain $C_1$–$C_4$ alkyl, straight or branched chain $C_1$–$C_4$ alkoxy; $CF_3$, $C(OH)_2CF_3$, $OCHF_2$, $OCF_3$, $NO_2$, $OCF_2CHF_2$, $N(CH_3)_2$, $CH_2N(CH_3)_2$, $CH_2NH_2$, $CH_2CH_2COOC_2H_5$, $C_6H_4$, $CH_2OH$, $CH_2OCH_3$, $COOCH_3$, $CH_2CH_2COOC_2H_5$, $OC_6H_5$, $OSO_2CH_3$, $SCH_3$, CN, $CH_2CN$ or tetrahydro-H-pyran-2-yl; and the salts, tautomers and optical isomers thereof.

* * * * *